(12) United States Patent
Nair et al.

(10) Patent No.: US 9,055,921 B2
(45) Date of Patent: *Jun. 16, 2015

(54) PLAQUE CHARACTERIZATION USING MULTIPLE INTRAVASCULAR ULTRASOUND DATASETS HAVING DISTINCT FILTER BANDS

(71) Applicant: Volcano Corporation, San Diego, CA (US)

(72) Inventors: Anuja Nair, Copley, OH (US); David Geoffrey Vince, Avon Lake, OH (US); Marja Pauliina Margolis, Coral Gables, FL (US); Kendall Rand Waters, Lakewood, OH (US)

(73) Assignee: Volcano Corporation, San Diego, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 13/867,822

(22) Filed: Apr. 22, 2013

(65) Prior Publication Data

US 2013/0245446 A1  Sep. 19, 2013

Related U.S. Application Data

(63) Continuation of application No. 12/875,390, filed on Sep. 3, 2010, now Pat. No. 8,425,423, which is a continuation of application No. 11/689,327, filed on Mar. 21, 2007, now Pat. No. 7,789,834.

(51) Int. Cl.
| | |
|---|---|
| *A61B 8/00* | (2006.01) |
| *A61B 8/08* | (2006.01) |
| *A61B 5/02* | (2006.01) |
| *A61B 8/12* | (2006.01) |
| *G01S 15/89* | (2006.01) |

(Continued)

(52) U.S. Cl.
CPC ........... *A61B 8/5207* (2013.01); *A61B 5/02007* (2013.01); *A61B 8/12* (2013.01); *A61B 8/4488* (2013.01); *G01S 7/52036* (2013.01); *G01S 15/8956* (2013.01); *A61B 8/085* (2013.01); *A61B 8/461* (2013.01)

(58) Field of Classification Search
CPC .... A61B 5/02007; A61B 8/12; A61B 8/4488; A61B 8/5207; A61B 8/085; A61B 8/461; G01S 15/8956; G01S 7/52036
USPC ........................................................ 600/443
See application file for complete search history.

(56) References Cited

U.S. PATENT DOCUMENTS

| | | |
|---|---|---|
| 5,261,280 A | 11/1993 | Matzuk |
| 6,108,572 A | 8/2000 | Panda et al. |

(Continued)

*Primary Examiner* — Katherine Fernandez
*Assistant Examiner* — Angela M Hoffa
(74) *Attorney, Agent, or Firm* — Haynes and Boone, LLP

(57) ABSTRACT

A system and method are disclosed that facilitate generating visual representations of characterized tissue based upon ultrasound echo information obtained from a portion of an imaged body. The system includes a first filter having a first filter band that is applied to a near range portion of the ultrasound echo information to render near range filtered echo information. A second filter, having a second filter band that covers a frequency range of the first filter band, is applied to a far range portion of the ultrasound echo information to render far range filtered echo information. The system furthermore includes a set of characterization criteria that are applied to the near and far range filtered echo information. The characterized near and far range image data are thereafter combined into a single tissue-characterization image.

20 Claims, 2 Drawing Sheets

(51) Int. Cl.
*G01N 9/24* (2006.01)
*G01S 7/52* (2006.01)

(56) References Cited

U.S. PATENT DOCUMENTS

| | | |
|---|---|---|
| 6,132,374 A | 10/2000 | Hossack et al. |
| 6,200,268 B1 | 3/2001 | Vince et al. |
| 6,494,839 B1 | 12/2002 | Averkiou |
| 6,516,667 B1 | 2/2003 | Broad et al. |
| 6,645,146 B1 | 11/2003 | Adams et al. |
| 7,074,188 B2 | 7/2006 | Nair et al. |
| 7,175,597 B2 | 2/2007 | Vince et al. |
| 7,789,834 B2 | 9/2010 | Nair et al. |
| 7,899,224 B2 | 3/2011 | Nair et al. |
| 8,425,423 B2 * | 4/2013 | Nair et al. ............ 600/443 |
| 2004/0122326 A1 | 6/2004 | Nair et al. |
| 2007/0149879 A1 | 6/2007 | Roundhill et al. |

* cited by examiner

| | Near Range | Far Range |
|---|---|---|
| Range (from lumen/tissue border) | 0-240 Microns | >240 Microns |
| Filter Band (for 20 MHz Transducer) | 12-26 MHz | 10-30 MHz |
| Characterization Criterion | Scheme I | Scheme II |

PLAQUE CHARACTERIZATION USING MULTIPLE INTRAVASCULAR ULTRASOUND DATASETS HAVING DISTINCT FILTER BANDS

CROSS-REFERENCE TO RELATED APPLICATION

This application is a continuation application of U.S. patent application Ser. No. 12/875,390, filed Sep. 3, 2010, now U.S. Pat. No. 8,425,423, which is a continuation application of U.S. patent application Ser. No. 11/689,327, filed Mar. 21, 2007, now U.S. Pat. No. 7,789,834, each of which is hereby incorporated by reference in its entirety.

FIELD OF THE INVENTION

The present invention generally relates to the field of imaging systems, and more particularly to intravascular imaging systems used to diagnose and treat vascular disease.

BACKGROUND OF THE INVENTION

The development of new medical technologies has provided an increasing number of options available to doctors for the diagnosis and treatment of cardiovascular diseases. The availability of such equipment has improved the ability of doctors and surgeons to detect and treat cardiovascular disease. Intravascular imaging technologies have enabled doctors to create and view a variety of images generated by a sensor inserted within a vasculature. Such images compliment traditional radiological imaging techniques such as angiography by providing images of the tissue within vessel walls rather than showing a two dimensional lumen image.

Intravascular ultrasound (IVUS) analysis finds particular application to a system and method for quantitative component identification within a vascular object including characterization of tissue. It should be appreciated that while the exemplary embodiment is described in terms of an ultrasonic device, or more particularly the use of IVUS data (or a transformation thereof) to characterize a vascular object, the present invention is not so limited. Thus, for example, using backscattered data (or a transformation thereof) based on ultrasound waves or even electromagnetic radiation (e.g., light waves in non-visible ranges) to characterize any tissue type or composition is within the spirit and scope of the present invention.

Imaging portions of a patient's body provides a useful tool in various areas of medical practice for determining the best type and course of treatment. Imaging of the coronary vessels of a patient by techniques involving insertion of a catheter-mounted probe (e.g., an ultrasound transducer array) can provide physicians with valuable information. For example, the image data indicates the extent of a stenosis in a patient, reveals progression of disease, helps determine whether procedures such as angioplasty or atherectomy are indicated or whether more invasive procedures are warranted.

In an ultrasound imaging system, an ultrasonic transducer probe is attached to a distal end of a catheter that is carefully maneuvered through a patient's body to a point of interest such as within a coronary artery. The transducer probe in known systems comprises a single piezoelectric crystal element that is mechanically scanned or rotated back and forth to cover a sector over a selected angular range. Acoustic signals are transmitted and echoes (or backscatter) from these acoustic signals are received. The backscatter data is used to identify the type or density of a scanned tissue. As the probe is swept through the sector, many acoustic lines are processed building up a sector-shaped image of the patient. After the data is collected, an image of the blood vessel (i.e., an IVUS image) is reconstructed using well-known techniques. This image is then visually analyzed by a cardiologist to assess the vessel components and plaque content. Other known systems acquire ultrasound echo data using a probe comprising an array of transducer elements.

In a particular application of IVUS imaging, ultrasound data is used to characterize tissue within a vasculature and produce images graphically depicting the content of the tissue making up imaged portions of a vessel. Examples of such imaging techniques for performing spectral analysis on ultrasound echoes to render a color-coded tissue map are presented in Nair et al. U.S. Pat. No. 7,074,188 entitled "System and Method of Characterizing Vascular Tissue" and Vince et al. U.S. Pat. No. 6,200,268 entitled "Vascular Plaque Characterization", the contents of which are incorporated herein by reference in their entirety, including any references contained therein. Such systems analyze response characteristics of ultrasound backscatter (reflected sound wave) data to identify a variety of tissue types found in partially occluded vessels including: fibrous tissue (FT), fibro-fatty (FF), necrotic core (NC), and dense calcium (DC).

When characterizing the response of tissue when exposed to ultrasound waves, parameter values are considered at a data point in an imaged field. Based upon response characteristics of known tissue types, tissue at the data point is assigned to a particular tissue type (e.g. necrotic core). In a known system, a data set is acquired using a single filter having a relatively wide band (e.g., 10-30 MHz for a 20 MHz IVUS transducer). The filtered raw digital ultrasound data is processed, and rendered tissue response data is applied to a tissue characterization criterion to render a tissue type for particular locations within an imaged blood vessel.

SUMMARY OF THE INVENTION

In accordance with the present invention a system and method are provided for characterizing plaque wherein distinct filter bands are applied to at least two sections (ranges) of echo signals received by an intravascular ultrasound probe. Furthermore, echo data obtained from a first/near range filter is processed according to a first tissue characterization criterion and echo data obtained from a second/far range filter is processed according to a second tissue characterization criterion. The distinct first and second filters and associated characterization criteria facilitate retaining as much information as possible about imaged tissue in the far range while limiting the presence of false image artifacts (e.g., NC speckle) near the lumen-tissue border. Such system and method is applicable, for example, to systems that perform spectral analysis on ultrasound echoes to render a color-coded tissue map.

BRIEF DESCRIPTION OF THE DRAWINGS

While the claims set forth the features of the present invention with particularity, the invention, together with its objects and advantages, may be best understood from the following detailed description taken in conjunction with the accompanying drawing of which:

DETAILED DESCRIPTION OF THE DRAWINGS

The disclosed system and method for characterizing plaque in blood vessels utilize at least two distinct filter bands to process ultrasound echoes received at different ranges of radial distance from the transducer probe (based upon the location of the lumen-tissue border). In an exemplary embodiment, a first filter, having a relatively narrow bandwidth, is applied to "near range" ultrasound echoes that arise from backscatter of ultrasound within a vessel lumen and near the lumen-tissue border. A second filter, having a relatively broad bandwidth that completely covers the band of the first filter, is applied to "far range" ultrasound echoes that arise from backscatter of ultrasound by tissue that extends beyond the "near range". In general, the first/near range filter renders echo information that has less noise content than echo information rendered by the second/far range filter. The filter bands are applied to near and far range echo information in a variety of ways including: analog circuitry and digital circuitry as well as hardware/firmware/software and combinations thereof.

Furthermore, first and second tissue classification criteria are applied to the filtered echo information rendered by the distinct first and second filters, respectively. A first tissue classification criterion, formulated according to samples observed using the first/near range filter, is applied to the filtered echo data rendered by the relatively narrower first/near range filter to characterize near range plaque. The second tissue classification criterion, formulated according to samples observed using the second/far range filter, is applied to the filtered echo information rendered by the second/far range filter.

An exemplary IVUS (intravascular ultrasound) system includes an ultrasonic probe device mounted upon a flexible elongate member for insertion into vasculature. The system furthermore includes a computing device comprising memory for storing computer executable instructions associated with a plaque characterization application program and digitized ultrasound backscatter/echo data for rendering images graphically depicting characterized tissue/plaque in vessel cross-sections. In the detailed description of the exemplary embodiment that follows, like element numerals are used to describe like elements illustrated in one or more figures.

Figures 1, 2:
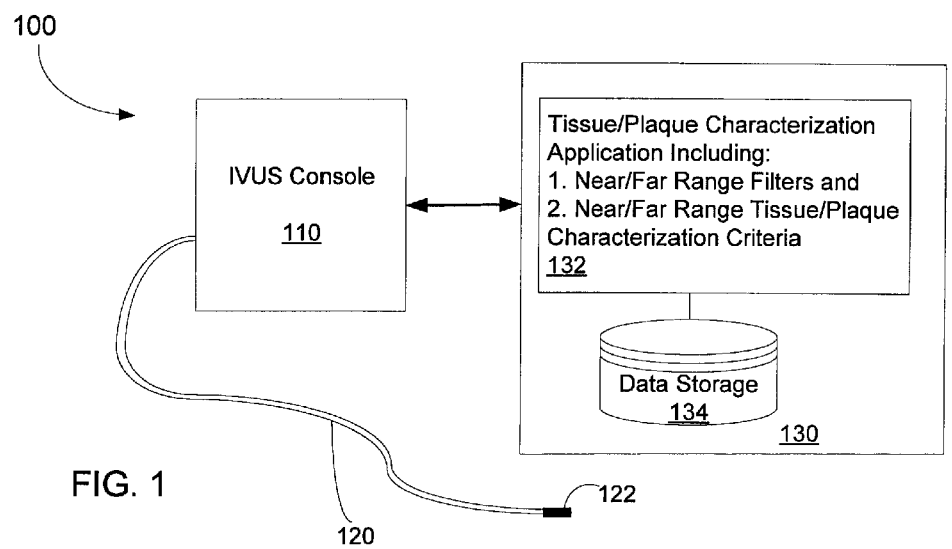
FIG. 1 illustrates a tissue-characterization system suitable for carrying out the disclosed tissue/plaque characterization scheme including multiple characterization criteria applied to multiple ranges of tissue/plaque depth associated with IVUS echo information.
FIG. 2 is a table identifying related characteristics for a frequency signature-based tissue characterization scheme including first and second characterization criteria associated with near range and far range signal filters, respectively.

Turning initially to FIG. 1, a tissue/plaque characterization system 100 is schematically depicted. An intravascular ultrasound console 110 is communicatively coupled to an IVUS catheter 120. The IVUS catheter 120 comprises a distally mounted ultrasound transducer probe 122 that acquires backscatter data (e.g., IVUS data) from a blood vessel. In accordance with known IVUS catheters, the catheter 120 is maneuvered through a patient's body (e.g., via a femoral artery) to a point of interest. The transducer probe 122 is then controlled, via the console 110 to emit ultrasound pulses and thereafter receive echoes or backscattered signals reflected from vascular tissue/plaque and blood. Because different types and densities of tissue absorb and reflect the ultrasound pulse differently, the reflected data (i.e., IVUS data) signals transmitted back to the console 110 by the IVUS catheter 120, is converted by characterization software into images of vascular objects. It should be appreciated that the IVUS console 110 depicted herein is not limited to any particular type of IVUS console, and includes all ultrasonic devices known to those skilled in the art (e.g., In-Vision Gold and s5™ systems of Volcano Corporation). It should further be appreciated that the IVUS catheter 120 depicted herein is not limited to any particular type of catheter, and includes all ultrasonic catheters known to those skilled in the art. Thus, for example, a catheter having a single transducer (e.g., adapted for rotation) or an array of transducers (e.g., circumferentially positioned around the catheter) is within the spirit and scope of the present invention.

Known imaging applications executed on an IVUS console (e.g. console 110) or a communicatively coupled computing device (e.g., computing device 130), render a variety of image types from received echo information. A first type of imaging application converts ultrasound echo signal data into gray scale images reflecting the relative strength of the echo signal returned by the objects within the transducer probe 120's field of view. In such imaging applications, the relatively light and dark regions indicate different tissue types and/or densities.

Other imaging applications, such as a tissue/plaque characterization application 132 executed on the computing device 130 communicatively coupled to console 110, renders tissue/plaque type information based upon the spectral (i.e., frequency and power) characteristics of the echo information received by the console 110 from the catheter 120. The frequency information extracted from the echo information rendered by the catheter 120 is compared to the frequency response signatures associated with particular types of tissue/plaque to render a tissue/plaque characterization image. A data storage 134 stores the tissue/plaque characterization images rendered by the characterization application 132 from the echo information received from the console 110. The data storage 134 is, by way of example, any of a variety of data storage devices, including RAM, cache memory, flash memory, magnetic disks, optical disks, removable disks, SCSI disks, IDE hard drives, tape drives, optically encoded information discs (e.g., DVD) and all other types of data storage devices (and combinations thereof, such as RAID devices) generally known to those skilled in the art.

In the illustrative example, the tissue/plaque characterization application 132 exists as a single application comprising one or more components. However, in other embodiments, the characterization application comprises multiple applications executed on one or more computing devices (including multiple processor systems as well as groups of networked computers). Thus, the number and location of the components depicted in FIG. 1 are not intended to limit the present invention, and are merely provided to illustrate the environment in which an exemplary system operates. Thus, for example, a computing device having a plurality of data storage devices and/or a remotely located characterization application (either in part or in whole) is within the spirit and scope of the present invention.

In accordance with an illustrative embodiment, the characterization application 132 utilizes two distinct near/far range filters and tissue/plaque characterization criteria when generating an image identifying types of tissue/plaque present in a vessel cross-section based upon frequency analysis of ultrasound echo information. Turning to FIG. 2, an exemplary two-filter/two-classification criteria tissue/plaque characterization scheme is summarized for a 20 MHz transducer (i.e., a transducer that emits ultrasound at a center frequency of 20 MHz). As depicted, by way of example, in the table presented in FIG. 2, a first characterization criterion (Scheme 1) is applied to echo information associated with a near range that radially extends 240 microns into tissue/plaque from the lumen-tissue border of a vessel. The echo information in the near range passes through a first filter having a relatively narrow band (e.g., about 12-26 MHz or narrower) prior to application of the first characterization criterion. The second characterization criterion (Scheme 2) is applied to echo information associated with a far range that begins at a depth/distance where the near range ends at the 240 micron depth in the tissue/plaque where the near range ends. The echo information in the far range passes through a second filter having a relatively broad band (e.g., about 10-30 MHz). The second filter's band completely covers the frequency range of the first filter's band.

It is explicitly noted that the above example is provided for an exemplary 20 MHz stationary 64-element array transducer assembly. However, other embodiments include a different transducer (e.g., a 45 MHz single rotating element IVUS probe), a different set of criteria, and associated border depth and filter bands. Furthermore, each of the exemplary filter bands will differ in accordance with alternative exemplary embodiments.

As those skilled in the art will readily appreciate, the characterization criteria will differ in accordance with differences in a variety of factors. Examples of such factors include, for example: the near/far range border depth (e.g., 240 microns), the frequency of the transducer (e.g., 20 MHz), the filter bands, and the types of tissue characterized, etc. However, in accordance with exemplary embodiments, the factors and corresponding criteria are designated to overcome at least one of the two following false tissue characterization artifacts: (1) the false identification of necrotic core (NC) speckle at the lumen-tissue boundary in a vessel that is prone to acute rupture; and (2) excessive identification of NC speckle in dense calcium (DC). In the illustrative example, both types of false identification are reduced by the combination of range/filter characteristics and generating first and second tissue/plaque classification criteria for near and far range tissue/plaque classification. The differences between the two characterization criteria are generally universal and arise from both the different ranges of echo signal information and the applied filter bands.

The near/far border for designating the end of a first range and the beginning of a second range, 240 microns in the illustrative example, varies in alternative embodiments. The selection of a particular depth for the first range is potentially influenced by the type of transducer, the imaging application, and the purpose for which the images are being generated.

Furthermore, the band of the near range filter is modified in accordance with alternative embodiments. For example, in an alternative embodiment the near range filter band is 15-24 MHz. However, in each embodiment, the near range filter band is narrower than, and falls completely within, the far range filter band.

It is noted that the identification of distinct filters is intended to emphasize the presence of two distinct filter bands applied to different ranges of echo information. For example, in an exemplary embodiment two distinct filters apply each of the two distinct filter bands. However, in an alternative embodiment, a single, multiple/variable band filter applies differing filter bands to different ranges of echo signal information. Therefore, the near/far range filters are, in the alternative embodiment, a single filter that is configured in a first instance to apply a near range filter band to near range echo information, and configured in a second instance to apply a far range filter band to far range echo information.

Figure 3:
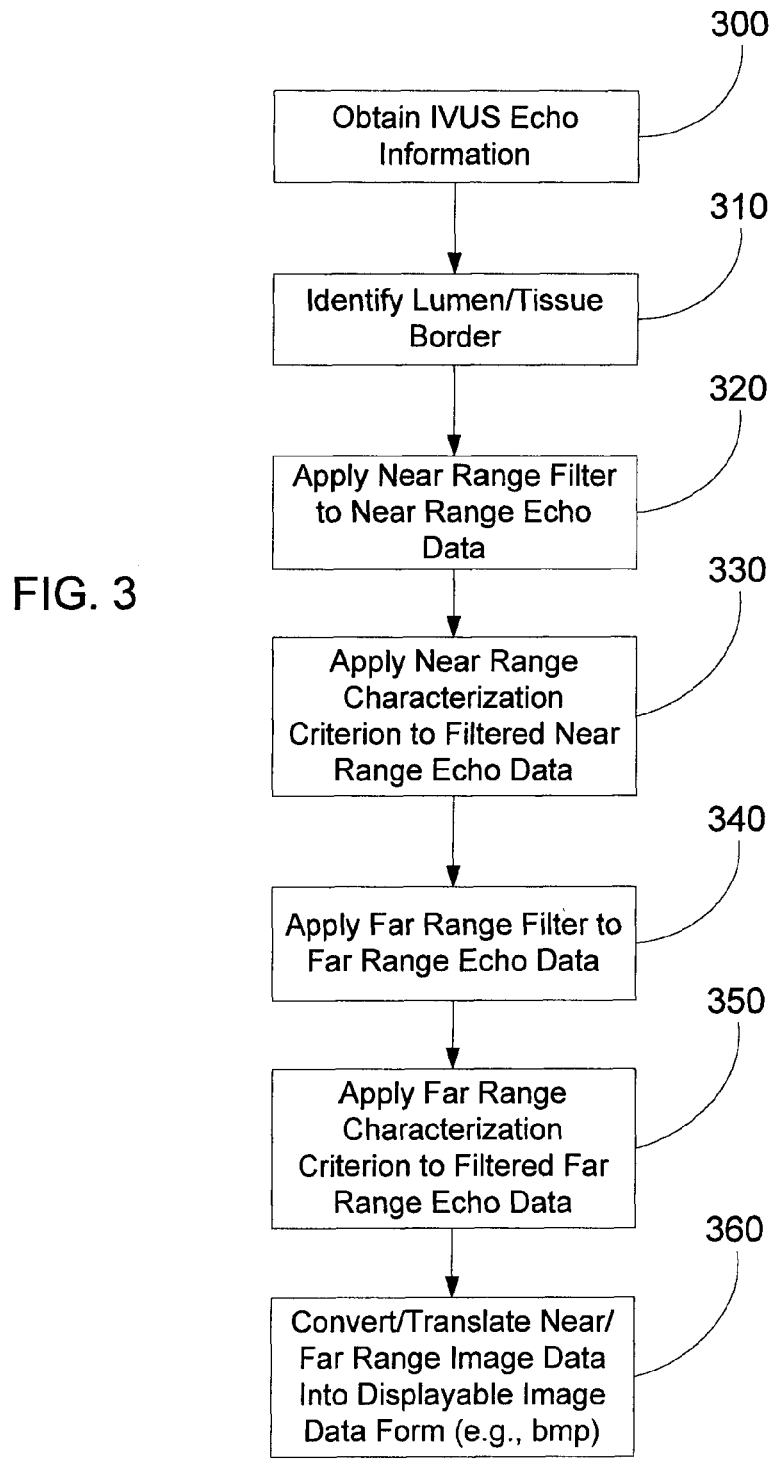
FIG. 3 is a flowchart summarizing an exemplary set of steps for applying first and second characterization criteria to near and far range echo information in accordance with an illustrative multiple characterization criteria scheme.

Having described an exemplary system including near/far range filters and associated criteria, attention is directed to FIG. 3 wherein a set of steps summarize an exemplary method for generating a blood vessel cross-section image that graphically depicts characterized tissue/plaque using the aforementioned dual filters and tissue classification criteria. Initially, during step 300, a set of IVUS echo information is obtained for a blood vessel cross section. Thereafter, at step 310 a lumen-tissue border is identified for each radial direction around the transducer probe (e.g. probe 122) that obtained the ultrasound echo information. Thereafter, during step 320 the first/near range filter is applied to near range echo information provided by the IVUS console 110. The near range echo data corresponds to a portion of each echo signal segment that begins at the lumen-tissue border and ends at the near/far range border depth (e.g. 240 microns from the lumen-tissue border). Thereafter, during step 330 a near range tissue/plaque characterization criterion is applied to the filtered near range echo information rendered during step 320. Thus, during step 330 a near range two-dimensional tissue characterization image is created that begins at the lumen-tissue border and extends to a depth of the near/far range border (e.g., 240 microns). The near range image is stored in the data storage 134.

During step 340 the second/far range filter is applied to the far range echo information provided by the IVUS console 110. In the illustrative example, the far range echo information is the remaining/distant portion of each echo signal segment that was not processed during steps 320 and 330. Thereafter, during step 350 a far range tissue/plaque characterization criterion is applied to the filtered far range echo information rendered during step 340. Thus, during step 350, a far range two-dimensional tissue characterization image is created that begins at the near/far range border. The far range image is stored in the data storage 134. Upon completion of step 350, the tissue/plaque characterization application has generated a complete image from two distinctly processed near/far range echo information sets. It is noted that while two filters and criteria are used in the illustrative example, in alternative embodiments three or more filters and/or criteria are used to render a complete image of a region of interest.

Finally, during step 360, the complete image is converted/translated into appropriate image data for display on a graphical output device. As those skilled in the art will readily appreciate the form of the image data will vary in accordance with the form of storage file and intended use (e.g., tif, pdf, bmp, jpeg etc.). Thus, the manner in which the data stored will vary in accordance with various alternative embodiments.

It is noted that while the illustrative embodiment discloses the use of two ranges, filters and criteria, in alternative embodiments more ranges, filter bands, and/or associated criteria are used. It is also noted that while each range is assigned a dedicated filter band and characterization criterion, in alternative embodiments two ranges share a single filter or alternatively a single characterization equation—though such alternative embodiments will include at least two distinct filter bands or two distinct characterization criteria that are applied to at least two different ranges. For example, a single filter band renders data in two ranges that are processed according to two distinct characterization criteria. Alternatively, two filter bands are applied to near and far range data, and the two distinct filtered data sets are processed according to a single characterization criterion.

Furthermore, the illustrative embodiments are directed to characterizing vascular tissue/plaque. In alternative embodiments the disclosed multiple filters/criteria arrangement are incorporated into characterization applications for characterizing: non-vascular cancerous tissue (cancerous, benign), from the prostate, breast or other parts of the body. Also myocardial tissue is identifiable using the above-described arrangement (e.g., healthy myocardial tissue, diseased myocardial tissue, ablated myocardial tissue, unablated myocardial tissue. Other vascular tissue is similarly characterized including: blood, thrombus, organized thrombus, unorganized thrombus, thrombus under an intimal flap, fibrous cap of an occlusive thrombus, fibro-lipidic tissues, calcified necrotic tissues, collagen, cholesterol, compositional structures (lumen, vessel wall, medial-adventitial boundary, etc.). The system is also potentially used to identify materials found in patients including, stent materials.

Systems and their associated components have been described herein above with reference to exemplary embodiments of the invention including their structures and techniques. It is noted that the present invention is implemented in computer hardware, firmware, and software in the form of computer-readable media including computer-executable instructions for carrying out the described functionality. In view of the many possible embodiments to which the principles of this invention may be applied, it should be recognized that the embodiments described herein with respect to the drawing figures are meant to be illustrative only and should not be taken as limiting the scope of invention. Therefore, the invention as described herein contemplates all such embodiments as may come within the scope of the following claims and equivalents thereof.

What is claimed is:

1. A method of characterizing tissue, comprising:
   collecting ultrasound echo information from a portion of an imaged body;
   applying a first filter band of a filter to a near range portion of the ultrasound echo information to render near range filtered echo information, the filter having the first filter band and a second filter band that completely covers and is broader than a frequency range of the first filter band;
   applying a first characterization criterion to the near range filtered echo information to render a near range tissue characterization image;
   applying the second filter band of the filter to a far range portion of the ultrasound echo information to render far range filtered echo information;
   applying at least one of the first and a second characterization criterion to the far range filtered echo information to render a far range tissue characterization image; and
   displaying an image based on the near range tissue characterization image and the far range tissue characterization image.

2. The method of claim 1, wherein the first and second characterization criteria include frequency and power response characteristics of the near and far range filtered echo information.

3. The method of claim 1, wherein the tissue is vascular tissue.

4. The method of claim 3, wherein the tissue comprises plaque.

5. The method of claim 1, wherein the first filter band is about 12 to 26 MHz.

6. The method of claim 1, wherein the ultrasound echo information is rendered from a 20 MHz transducer.

7. The method of claim 1, wherein the ultrasound echo information is rendered from a 45 MHz transducer.

8. The method of claim 1, further comprising combining the near range and the far range tissue characterization image information to render the image.

9. The method of claim 1, further comprising applying a third filter band of the first filter to a third range of echo information.

10. The method of claim 9, further comprising applying at least one of the first, the second, and a third characterization criterion to the third range filtered echo information to render a third range tissue characterization image.

11. A non-transitory computer-readable medium including computer-executable instructions facilitating characterizing tissue, the computer-executable instructions when executed by a computing device, perform a set of steps comprising:
    receiving ultrasound echo information from a portion of an imaged body;
    applying a first filter band of a filter, to a near range portion of the ultrasound echo information to render near range filtered echo information, the filter having the first filter band and a second filter band that completely covers and is broader than a frequency range of the first filter band;
    applying a first characterization criterion to the near range filtered echo information to render a near range tissue characterization image;
    applying the second filter band of the filter to a far range portion of the ultrasound echo information to render far range filtered echo information;
    applying at least one of the first and a second characterization criterion to the far range filtered echo information to render a far range tissue characterization image; and
    displaying an image based on the near range tissue characterization image and the far range tissue characterization image.

12. The non-transitory computer-readable medium of claim 11, wherein the first and second characterization criteria include frequency and power response characteristics of the near and far range filtered echo information.

13. The non-transitory computer-readable medium of claim 11, wherein the tissue is vascular tissue.

14. The non-transitory computer-readable medium of claim 13, wherein the tissue comprises plaque.

15. The non-transitory computer-readable medium of claim 11, further comprising combining the near range and the far range tissue characterization image information to render the image.

16. A system for generating visual representations of characterized tissue based upon ultrasound echo information obtained from a portion of an imaged body, comprising:
    a filter including:
        a first filter band configured to render near range filtered echo information from a near range portion of the ultrasound echo information; and
        a second filter band configured to render far range filtered echo information from a far range portion of the ultrasound echo information, the second filter band completely covering and being broader than a frequency range of the first filter band;
    a set of characterization criteria including:
        a first characterization criteria for application to the near range filtered echo information to render a near range tissue characterization image, and
        a second characterization criterion for application to the far range filtered echo information to render a far range tissue characterization image; and
    a display device configured to display an image based on the near range tissue characterization image and the far range tissue characterization image.

17. The system of claim 16 wherein the first and second characterization criteria include frequency and power response characteristics of the near and far range filtered echo information.

18. The system of claim 16, wherein the tissue is vascular tissue.

19. The system of claim 16, wherein the first filter band is about 12 to 26 MHz.

20. The system of claim 16, wherein the set of characterization criteria are applied by a processing system in communication with an imaging device.

* * * * *